United States Patent
Korukonda et al.

(10) Patent No.: US 12,390,190 B2
(45) Date of Patent: Aug. 19, 2025

(54) ACOUSTIC REGISTRATION OF INTERNAL AND EXTERNAL ULTRASOUND PROBES

(71) Applicant: KONINKLIJKE PHILIPS N.V., Eindhoven (NL)

(72) Inventors: Sanghamithra Korukonda, Seattle, WA (US); Francois Guy Gerard Marie Vignon, Andover, MA (US); Ameet Kumar Jain, Boston, MA (US); Emil George Radulescu, Ossining, NY (US); Jean-Luc Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1447 days.

(21) Appl. No.: 16/094,104

(22) PCT Filed: Apr. 6, 2017

(86) PCT No.: PCT/EP2017/058173
§ 371 (c)(1),
(2) Date: Oct. 16, 2018

(87) PCT Pub. No.: WO2017/182278
PCT Pub. Date: Oct. 26, 2017

(65) Prior Publication Data
US 2019/0090842 A1    Mar. 28, 2019

Related U.S. Application Data

(60) Provisional application No. 62/324,640, filed on Apr. 19, 2016.

(51) Int. Cl.
*A61B 8/00* (2006.01)
*A61B 8/12* (2006.01)
(Continued)

(52) U.S. Cl.
CPC .............. *A61B 8/4263* (2013.01); *A61B 8/12* (2013.01); *A61B 8/4245* (2013.01);
(Continued)

(58) Field of Classification Search
CPC .......... A61B 8/4477; A61B 2034/2063; A61B 8/4283; A61B 8/4245; A61B 8/4263;
(Continued)

(56) References Cited

U.S. PATENT DOCUMENTS

| 4,249,539 | A | * | 2/1981 | Vilkomerson | ....... | A61B 8/0833 |
| | | | | | | 600/461 |
| 5,349,262 | A | * | 9/1994 | Grenon | ............... | G01S 15/8927 |
| | | | | | | 310/334 |

(Continued)

FOREIGN PATENT DOCUMENTS

| JP | 2001516075 A | 9/2001 |
| WO | 2012172458 A1 | 12/2012 |
| WO | 2013038217 A1 | 3/2013 |

OTHER PUBLICATIONS

University of Washington Lecture 6—Ultrasound; https://courses.washington.edu/bioen508/Lecture6-US.pdf (Year: 2007).*
(Continued)

*Primary Examiner* — Chao Sheng

(57) ABSTRACT

An acoustically registerable probe includes a transducer (212) to generate acoustic pulses, and a beamformer (222) coupled to the transducer to adjust a field of view of the acoustic pulses. The transducer is configured to iteratively send and receive acoustic energy with a decremented field of view angles to identify a position of the transducer (216) to other transducers and to reveal positions of the other transducers to the transducer through a medium carrying the acoustic pulses to register the transducer to the other transducers coupled to the medium.

11 Claims, 7 Drawing Sheets

(51) Int. Cl.
*G01S 5/20* (2006.01)
*G01S 15/89* (2006.01)

(52) U.S. Cl.
CPC .......... *A61B 8/4281* (2013.01); *A61B 8/4477* (2013.01); *A61B 8/4488* (2013.01); *A61B 8/5207* (2013.01); *A61B 8/5253* (2013.01); *G01S 5/20* (2013.01); *G01S 15/899* (2013.01); *A61B 8/5238* (2013.01); *A61B 8/5261* (2013.01)

(58) Field of Classification Search
CPC ....... A61B 8/12; A61B 8/4281; A61B 8/5207; A61B 8/5253; A61B 8/5238; A61B 8/5261; G01S 5/20; G01S 15/899
See application file for complete search history.

(56) References Cited

U.S. PATENT DOCUMENTS

| | | | |
|---|---|---|---|
| 6,128,958 A | 10/2000 | Cain | |
| 9,282,946 B2 | 3/2016 | Vignon | |
| 2004/0225218 A1* | 11/2004 | Guracar | G01S 15/8911 600/443 |
| 2006/0009695 A1* | 1/2006 | Mathew | G16H 40/67 600/437 |
| 2012/0071758 A1* | 3/2012 | Lachaine | A61N 5/1049 600/443 |
| 2012/0237102 A1* | 9/2012 | Savitsky | G09B 23/286 382/131 |
| 2013/0041252 A1* | 2/2013 | Vignon | A61B 8/5207 600/424 |
| 2014/0276003 A1 | 9/2014 | Wang | |
| 2016/0242746 A1* | 8/2016 | Rao | A61B 6/56 |

OTHER PUBLICATIONS

Ortega et al. Automatic Definition of an Anatomic Field of View for Volumetric Cardiac Motion Estimation at High Temporal Resolution; Published on Jul. 24, 2017; Applied Sciences 2017, 7, 752 (Year: 2017).*

Merdes, Christine L. et al "Locating a Catheter Transducer in a Three-Dimensional Ultrasound Imaging Field", IEEE Transactions on Biomedical Engineering, vol. 48, No. 12, Dec. 2001.

Mung, Jay et al "Design and in vitro Evaluation of a Real-Time Catheter Localization System using Time of Flight Measurements from Seven 3.5 MHz Single Element Ultraound Transducers towards Abdominal Aortic Aneurysm Procedures", Ultrasonics, Vpl. 51, pp. 768-775. 2011.

Szmigielski, Cezary et al "Real-Time 3D Fusion Echocardiography", JACC: Cardiovascular Imaging, vol. 3, No. 7, 2010, pp. 682-690.

* cited by examiner

ACOUSTIC REGISTRATION OF INTERNAL AND EXTERNAL ULTRASOUND PROBES

BACKGROUND

Technical Field

This disclosure relates to ultrasound devices and more particularly to acoustic registration of ultrasound probes.

Description of the Related Art

Several technologies may be employed for spatially registering ultrasound probes for the purpose of image fusion between the images generated using the probes. These technologies include image-based image registration, mechanical sweeping devices (e.g., a manual sweeping, brachytherapy stepper, intravenous ultrasound (IVUS) pullback, early generations "rocking" 3D imaging probes, etc.), electromagnetic (EM) tracking, optical tracking, fiber-optic tracking (Fiber-Optical Real Shape™), optical-position-sensing-enabled ultrasound imaging, etc.

These technologies may suffer from issues that may include some of the following. For example, image-based registration is computationally intensive and is not real-time due to computational delay. Mechanical devices are restrictive with respect to the range of probe motion, positions allowed and tracking accuracy. EM tracking has the disadvantage of requiring set up and calibration of an external tracking system. In addition, tracking accuracies (typically a few mm) are degraded by the presence of metallic objects. Optical (external, interferometric, fiber-optic) are high resolution but require the setup of an external system, and may be expensive.

SUMMARY

In accordance with the present principles, an acoustically registerable probe includes a transducer to generate acoustic pulses, and a beamformer coupled to the transducer to adjust a field of view of the acoustic pulses. The transducer is configured to iteratively send and receive acoustic energy with a decremented field of view angles to identify a position of the transducer to other transducers and to reveal positions of the other transducers to the transducer through a medium carrying the acoustic pulses to register the transducer to the other transducers coupled to the medium.

A system for acoustically registering probes includes a first probe coupled to a medium to transmit and receive acoustic pulses and a second probe coupled to the medium to transmit and receive acoustic pulses such that when the first and second probes are in a field of view of each other, registration is provided by acoustic communication therebetween. The first and second probes are configured to iteratively send and receive acoustic energy with decremented field of view angles to identify a position of each other through the medium carrying the acoustic pulses to register the first and second probes in a common coordinate system.

A method for acoustically registering probes includes transmitting a first acoustic pulse at a first field of view angle from a first probe; receiving the first acoustic pulse at a second probe to measure time of flight and signal strength of the first pulse; transmitting a second acoustic pulse at a second narrower field of view angle than the first field of view angle from the second probe; receiving the second acoustic pulse at the first probe to measure time of flight and signal strength of the second pulse; and computing positions of the first probe and the second probe based upon measured times of flight and signal strengths to register the first probe and the second probe to a common coordinate system.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
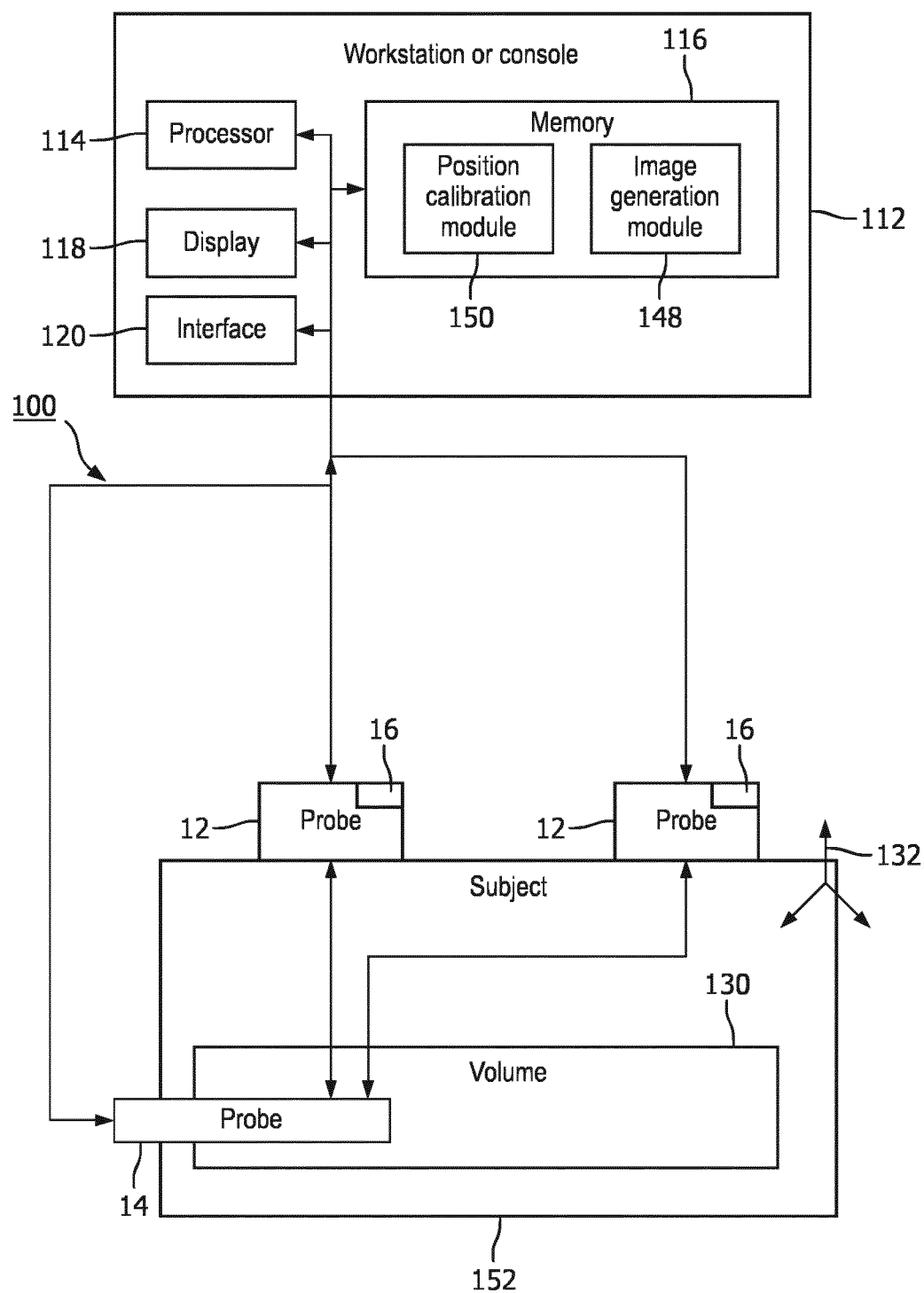
FIG. 1 is a block/flow diagram showing a system for acoustically registering ultrasound probes in accordance with one embodiment.

In accordance with the present principles, simple and accurate tracking methods and systems are provided for two or more ultrasound probes concurrently employed. The present embodiments are based on the use of the same ultrasound waves employed to form pulse-echo images from a tracked probe(s). In useful embodiments, the tracking is low-cost and does not interfere with existing workflows. In one embodiment, multiple ultrasound probes are employed in conjunction with one another to provide improved anatomy visualization. These probes can be registered acoustically with one another and to a common coordinate system to provide a comprehensive image of an area of interest or greater detail of a specific region within the area of interest. In one example, in the discipline of echocardiography, internal transesophageal echo (TEE) can provide detailed small fields of view within a heart while an external transthoracic echo (TTE) probe can provide anatomical context for improved visualization. Registration of the multiple probes is provided using ultrasound signaling for synchronized acquisition and visualization.

Ultrasound positioning of intra-body instruments equipped with transducers are employed to track 3D positions of one or more ultrasound transmitter/receivers. This can be used to determine and track a 2D or 3D pose (e.g., position and orientation) of one or several probes with respect to each other. Once registered to a common coordinate system, image processing may be employed to expand the visualization capabilities of the system. The present principles enable real-time registration of multiple ultrasound probes in space and time permitting multi-perspective imaging. This leads to improved visualization of soft tissue anatomy and reduced artifacts from device shadowing or reverberation. The present principles can be applied to any combination of ultrasound probes and for a multitude of applications such as, e.g., cranial imaging, breast imaging, renal imaging, etc.

It should be understood that the present invention will be described in terms of medical instruments; however, the teachings of the present invention are much broader and are applicable to any acoustic instruments. In some embodiments, the present principles are employed in tracking or analyzing complex biological or mechanical systems. In particular, the present principles are applicable to internal and/or external tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for acoustically registering two or more probes is illustratively shown in accordance with one embodiment. System 100 may include one or more workstations or consoles 112 associated with each probe 12, 14. In one embodiment, a single workstation 112 may be employed for multiple probes 12, 14. Workstation 112 preferably includes one or more processors 114 and memory 116 for storing programs and applications. Memory 116 stores programs for acoustically registering one or more ultrasound probes with respect to each other. A position calibration module 150 is stored in memory 116 and is configured to register all ultrasound probes 12 and 14 to a single coordinate system. In addition, the position calibration module 150 updates new positions and orientations of the probes 12 as they dynamically change positions during a procedure or training session. While FIG. 1 depicts that all probes 12, 14 can be controlled by a single ultrasound system or workstation 112 such that all beam transmission and reception can be performed synchronously, the present principles may also include multiple beam transmission and reception systems that report positions to a single or distributed position calibration module 150.

In one embodiment, multiple ultrasound probes 12, 14 are employed in conjunction with one another to provide improved anatomy visualization. For example, in echocardiography, an internal transesophageal echo (TEE) probe 14 can provide detailed small fields of view within a heart (volume 130) while an external transthoracic echo (TTE) probes 12 can provide anatomical context for improved visualization. These probes 12, 14 can be registered to each other to using ultrasound signaling therebetween to synchronize acquisition and visualization.

The registration process relies on signal exchanges between the probes 12, 14. The position calibration module 150 computes the probes' positions based on transmitted/received signals between the probes 12, 14. The locations are updated by the position calibration module 150 to generate transformation matrices or other position indicators to register multiple image volumes in a common reference space or coordinate system 132 for incoherent volume compounding or side-by-side display.

Image configuration preferences may be input by a user into the system 100 through an image generation module 148. The image generation module 148 may stitch or fuse images obtained from multiple probes 12, 14 to create a single view or may generate more detailed views of a particle area or areas of interest sequentially or concurrently (multi-views).

In one embodiment, the probe 14 may be positioned internally within the volume 130 within a subject 152, while the probes 12 are positioned externally on the subject 152. External probes 12 are more easily tracked in the common space 132. The external probes 12 can be registered to one another using one or more methods. These methods may include spatial encoding, electromagnetic (EM) tracking, or other methods to generate a standard reference coordinate space 132. Such tracking is optional since the probes 12, 14 can be acoustically registered in accordance with aspects of the present principles. In one example, if EM tracking is employed, one or more probes 12 may include an EM sensor 16 that tracks movement of the probes 12 in an EM field created by an EM generator (not shown). With the positions of the external probes 12 known, the internal probe(s) 14 transmit a series of directed acoustic pulses, e.g., over a large field of view, while the probes 12 passively receive the pulses. This is repeated with the external probes 12 actively transmitting while the internal probe(s) passively receive.

Based on signal strength, time of flight and/or other acoustic wave characteristics of the received echoes, the probes 12, 14 can identify a rough direction in which the other probes 12, 14 are located. In the next iteration or cycle, focused pulses will again be transmitted, but over a smaller and more directed field of view. This can be repeated iteratively and synchronously until each probe has zeroed in on the location of the other probes 12, 14. The position calibration module 150 stores the positions and orientations of each probe 12, 14 at each iteration. Once the locations (e.g., distance and direction) of the probes 12, 14 are known with respect to one another, a coordinate transformation can be generated by the position calibration module 150 to register all probes in the same coordinate space 132.

The probes 12, 14 need to include overlap in their operating bandwidth to ensure that the probes 12, 14 can acoustically recognize one another. For example, the bandwidths of the probes 12, 14 preferably include a same central frequency as the other probes such that the transmitted pulses can be detected. If the probes 12, 14 are to perform compounded imaging (e.g., two or more probes contributing to a single compound or stitched image) the probes 12, 14 need to be within imaging frustums of the each other.

In one embodiment, the external probes 12 may remain fixed and the internal probe 14 may be moved. However, the present principles are not limited to this configuration, and one or more probes may be fixed and one or more probes may be moving at any time. In a particularly useful embodiment, the external probes 12 may include transthoracic probes that remain fixed on a chest wall of the subject 152, while the internal probe of probes 14 can move within the volume 130 of the subject 152. If the internal probe is a TEE probe, the TEE probe may move up and down the gut, and at each position of the TEE probe, a re-registration may be needed. If the TEE probe (14) moves out of view of one of the external probes 12 (e.g., a TTE probe), another TTE probe (12) could be activated for the procedure, if it is in a better position (within view).

In one embodiment, the image generation module 148 may be configured to setup up different viewing configurations. These may include a single compound view, which combines received data from multiple probes, multiple pane views including separate images for each probe, fused images from the probes or any combination thereof. The images may be directly displayed or processed prior to display. The images can be displayed on a display device 118 for viewing the internal images of the subject 152. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

It should be understood that the present principles may be employed using different types of probes and different types of acoustic technologies (e.g., intravenous ultrasound (IVUS), endoscopic ultrasound (EUS), intracardiac echocardiography (ICE), endobronchial ultrasound (EBUS), TEE, TTE, etc. In some embodiments, probes 12, 14 may include a single element with an A-mode, M-mode, etc. scanner. The probes 12, 14 may image in Doppler™, SonoCT™ or other modes with any combination being displayed. The probes 12, 14 may employ combinations of any sensor technology, e.g., piezoelectric (PZT), capacitive micromachined ultrasonic transducers (cMUT), optical sensors, etc. in each probe 12, 14.

Figure 2A:
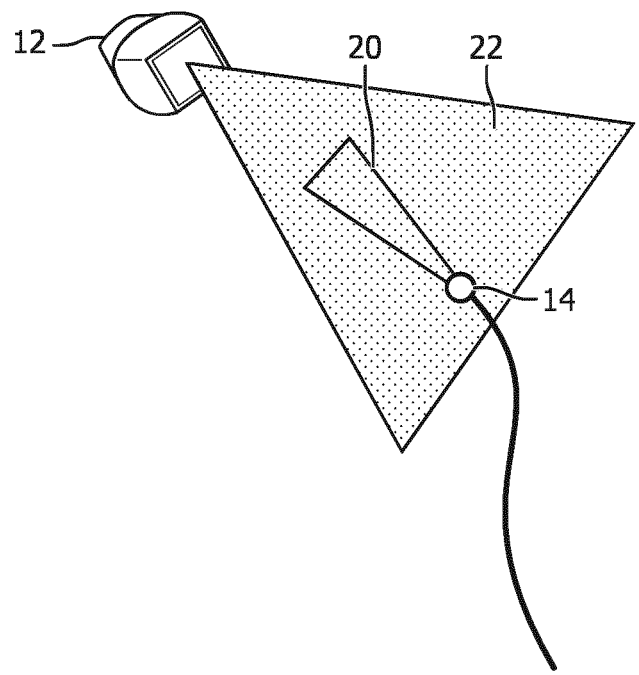
FIG. 2A is a diagram showing acoustic communication between an external and an internal probe for acoustically registering the probes in accordance with one embodiment.

Referring to FIG. 2A, the probe 12 may include a large external ultrasound probe and the probe 14 may include a smaller ultrasound probe (e.g., a 2D ICE). A 2D ICE image from probe 14 can be registered to probe 12 (e.g., a 3D TEE image). A subset or all individual elements of the probe 12 are tracked in the coordinate system of the probe 14 (or vice versa). Tracking of any single element of the probe 12 can be done using emitted signals from the probe 14. Focused beams 20, 22 between the probes 14 and 12 are transmitted and received by one another in sequence while altering the angular fields of view. The positions of the probes 12, 14 are revealed by analysis of: time of flight (yields range), and the angular information (yields beam directions and provides the signal strength). A position accuracy of 0.4 mm or less and angular accuracy of 1.2° or less can be achieved for elements separated by about 20 mm.

Each probe 12, 14 needs to be inside the field of view of the other probe (14, 12). While two elements, patches or beacons may be employed to estimate the pose and position of the ultrasound elements (probes) (two elements can define a vector in space that fully characterizes the six degrees of freedom (3 translations, 3 rotations) of the object), tracking more elements is beneficial for the robustness of the estimate. Once the relative positions and orientations of the probes 12, 14 are known, the images from both probes 12, 14 can be displayed in the same coordinate system. The individual images can be superimposed on a single display, with each probe providing a resolution in a small area or wider area.

Figure 2B:
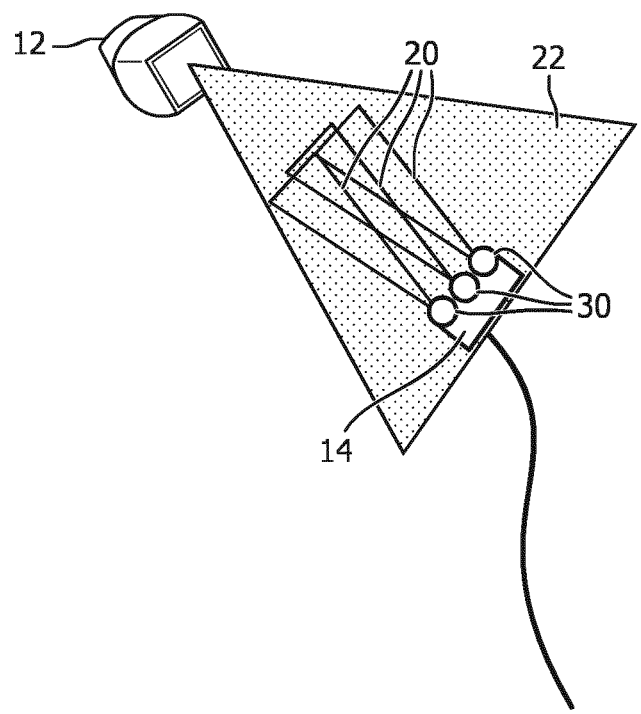
FIG. 2B is a diagram showing acoustic communication between probes where one probe includes multiple elements for acoustically registering the probes in accordance with another embodiment.

Referring to FIG. 2B, the probe 14 (and/or probe 12) may include a few discrete sensors/elements 30 doing, e.g., A-mode/M-mode single sensor imaging. The sensor positions are known for the given probe and the array arrangements of sensors/elements 30 makes time of flight, position and pose information more easily computed due to the known spatial relationships of the sensors 30 on the probe 14.

Figure 3:
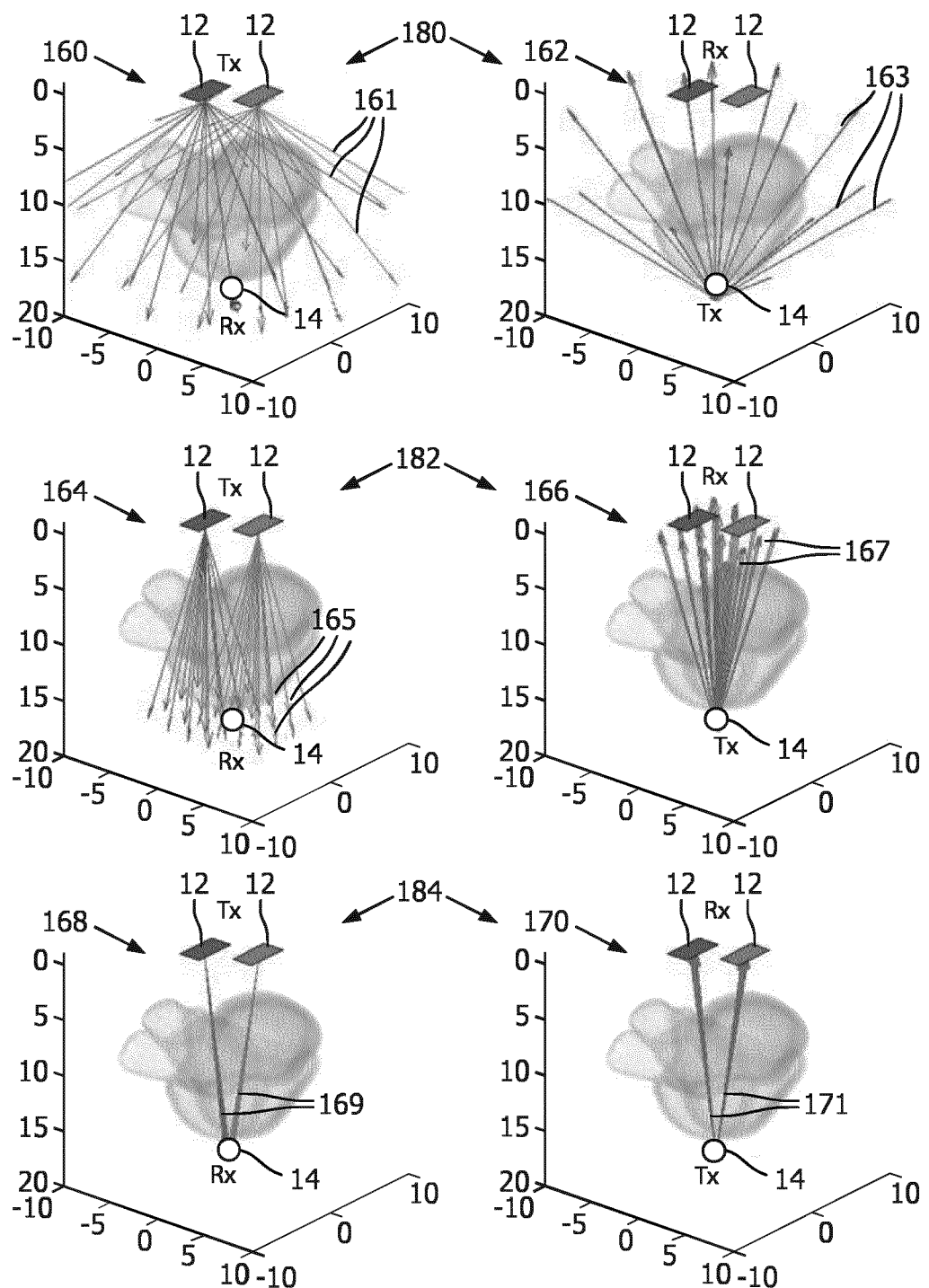
FIG. 3 is a diagram showing acoustic communication between probes for acoustically registering the probes in accordance with one embodiment.

Referring to FIG. 3, acoustic registration of multiple probes may include a single TEE probe 14 with multiple TTE probes 12 constituting of a large area TTE (or LATTE probe). As illustratively depicted in FIG. 3, a plurality of transthoracic and transesophageal probes are registered for, e.g., an interventional cardiology procedure. The registration process may include the following. A TEE probe 14 (e.g., a wire or catheter) is positioned within the esophagus or other volume in a subject, while two TTE probes 12 that are positioned on the chest wall in different intercostal spaces (e.g., between the ribs). These provide opposing groups of probes. The external probes 12 can be registered to one another using a spatial encoding, EM tracking, etc. to generate a standard reference coordinate space. In a first instance 160 of a first iteration 180, the TTE probes 12 transmit a series of directed acoustic pulses 161 over a large field of view, while the TEE probes 14 passively receive the pulses 161. The same process is repeated in instance 162, with the TEE probe 14 actively transmitting pulses 163 while the TTE probes 12 passively receive the pulses 163. Based on the strength and time of flight of the received echoes from the pulses 161 and 163, the probes 12 or 14 can identify a rough direction in which the other probes 14 or 12 are located.

In a next iteration 182, more focused pulses 165 and 167 are transmitted over a smaller and more directed field of view. In a first instance 164 of the iteration 182, the TTE probes 12 transmit a series of directed acoustic pulses 165 over a narrower field of view, while the TEE probes 14 passively receive the pulses 165. The same process is repeated in instance 166, with the TEE probe 14 actively transmitting pulses 167 while the TTE probes 12 passively receive the pulses 167. Based on the strength and time of flight of the received echoes from the pulses 165 and 167, the probes 12 or 14 can identify a direction in which the other probes 14 or 12 are located.

The process continues iteratively and synchronously until each probe has zeroed in on the location of the other probes. For example, in iteration 184, even greater focused pulses 169 and 171 are transmitted over a more directed field of view. In a first instance 168 of the iteration 184, the TTE probes 12 transmit a series of directed acoustic pulses 169 over a narrower field of view (e.g., 5-10 degrees per iteration, although other amounts may be employed), while the TEE probes 14 passively receive the pulses 169. The same process is repeated in instance 170, with the TEE probe 14 actively transmitting pulses 171 while the TTE probes 12 passively receive the pulses 171. Based on the strength and time of flight of the received echoes from the pulses 169 and 171, the probes 12 or 14 can further identify a direction in which the other probes 14 or 12 are located.

Once the location (e.g., distance and direction) of the probes 12, 14 is known with respect to one another, a coordinate transformation needed to register all probes in a same coordinate space is determined.

It should be understood that the present examples describe three iterations where the beam focus and field of view is adjusted; however, in some embodiments, a single iteration may be employed or a plurality of iterations may be employed depending on the application and the resolution needed. In addition, three probes are depicted; however, any number of probes 12 and/or probes 14 may be employed.

Figure 4:
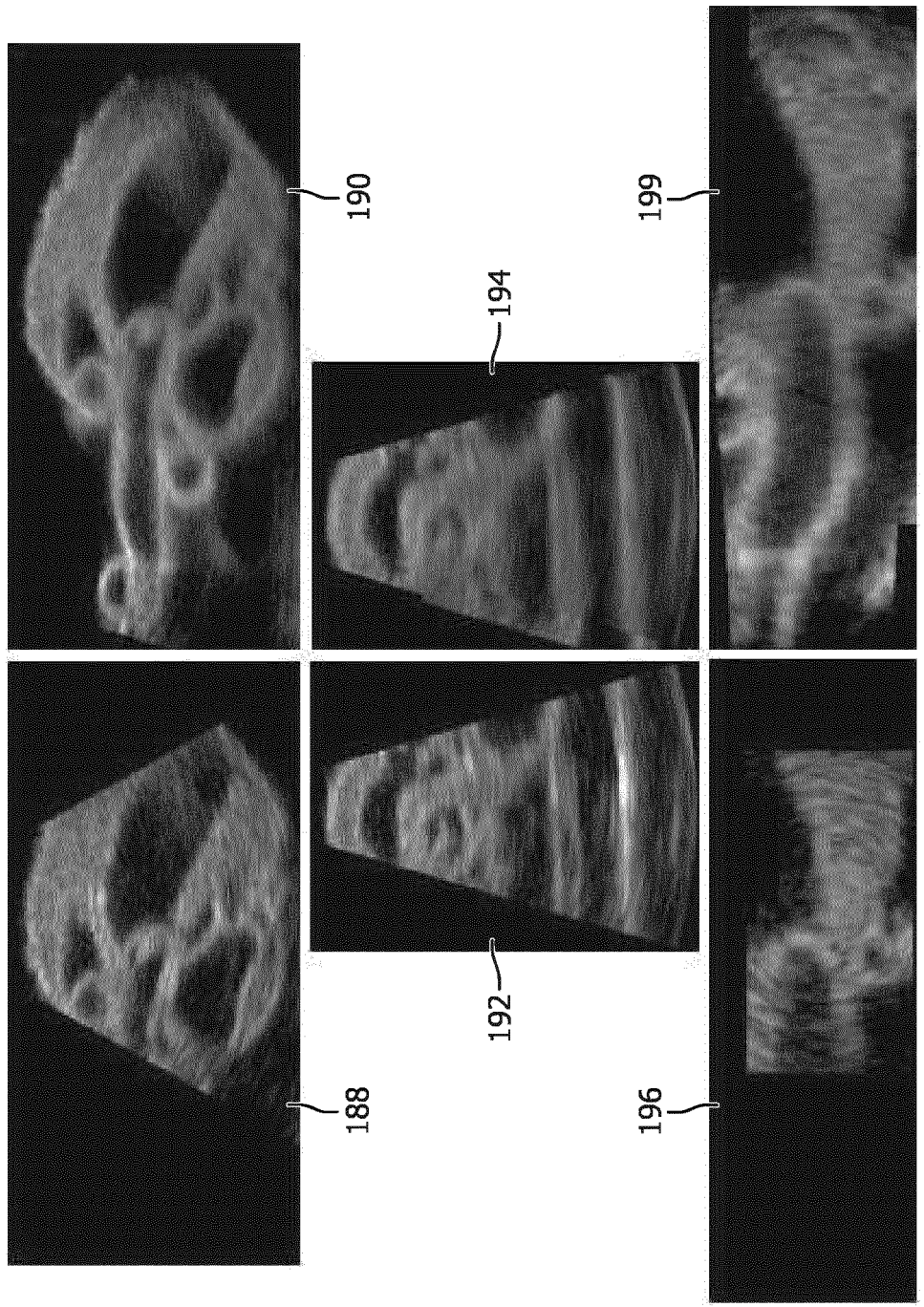
FIG. 4 shows ultrasound images having compound images obtained by fusing or stitching together image data from multiple probes in accordance with the present principles.

Referring to FIG. 4, six images 188-198 are illustratively shown of a heart phantom taken with multiple imaging probes in accordance with the present principles. Images 188, 192 and 196 depict single-view images of the heart phantom. The images 190, 194 and 198 show extended field of view (FOV), high quality images achieved by combining 6 images taken from different viewpoints separated in the azimuth direction. Images 188 and 190 show an azimuthal slice. Images 192 and 194 show an elevational slice. Images 196 and 198 show a transverse slice. The combination of several images from the TEE/TTE probes from different perspectives yields extended field of view imaging and the capability of spatial compounding for enhanced image quality in accordance with the present principles.

Real-time registration of multiple ultrasound probes in space and time permits multi-perspective imaging, which improves visualization of soft tissue anatomy and reduces artifacts from device shadowing or reverberation. The present principles can be applied to any combination of ultrasound probes and for a multitude of applications such as, e.g., cranial imaging, breast imaging, renal imaging, etc.

Figure 5:
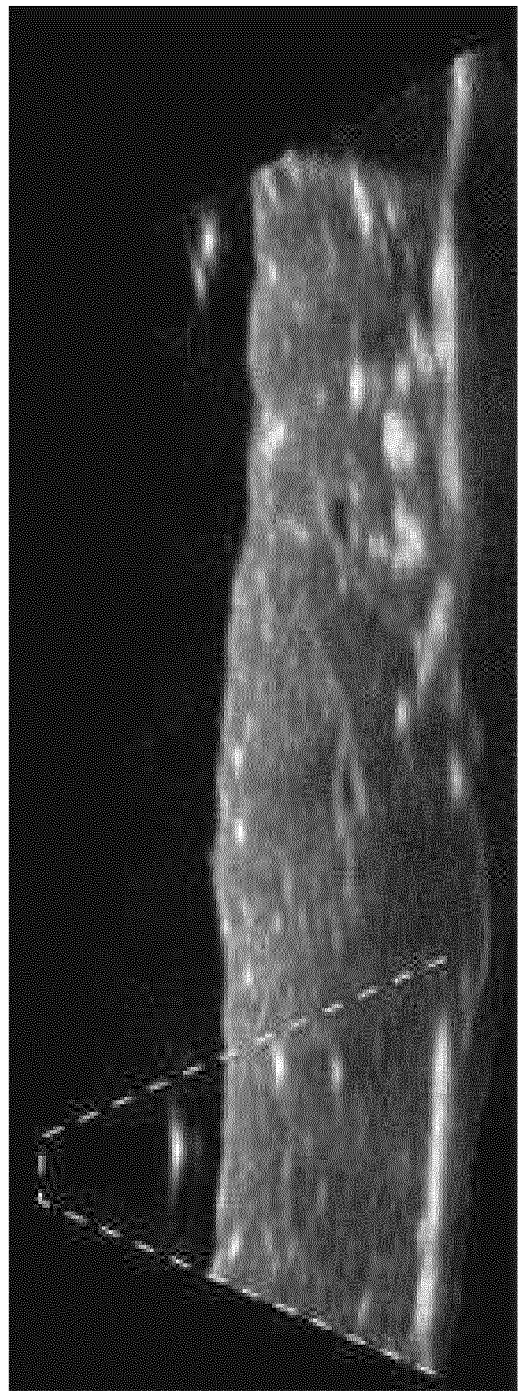
FIG. 5 shows ultrasound images stitched together from multiple probes to form a larger view in accordance with the present principles.

Referring to FIG. 5, multiple images from one probe can be stitched into a reference frame of the other probe over time to create a larger image 200 with a larger field of view. Alternately, the stitching may be employed to aid in seeing tissue motion over time (e.g., cardiac or lung motion).

Figure 6:
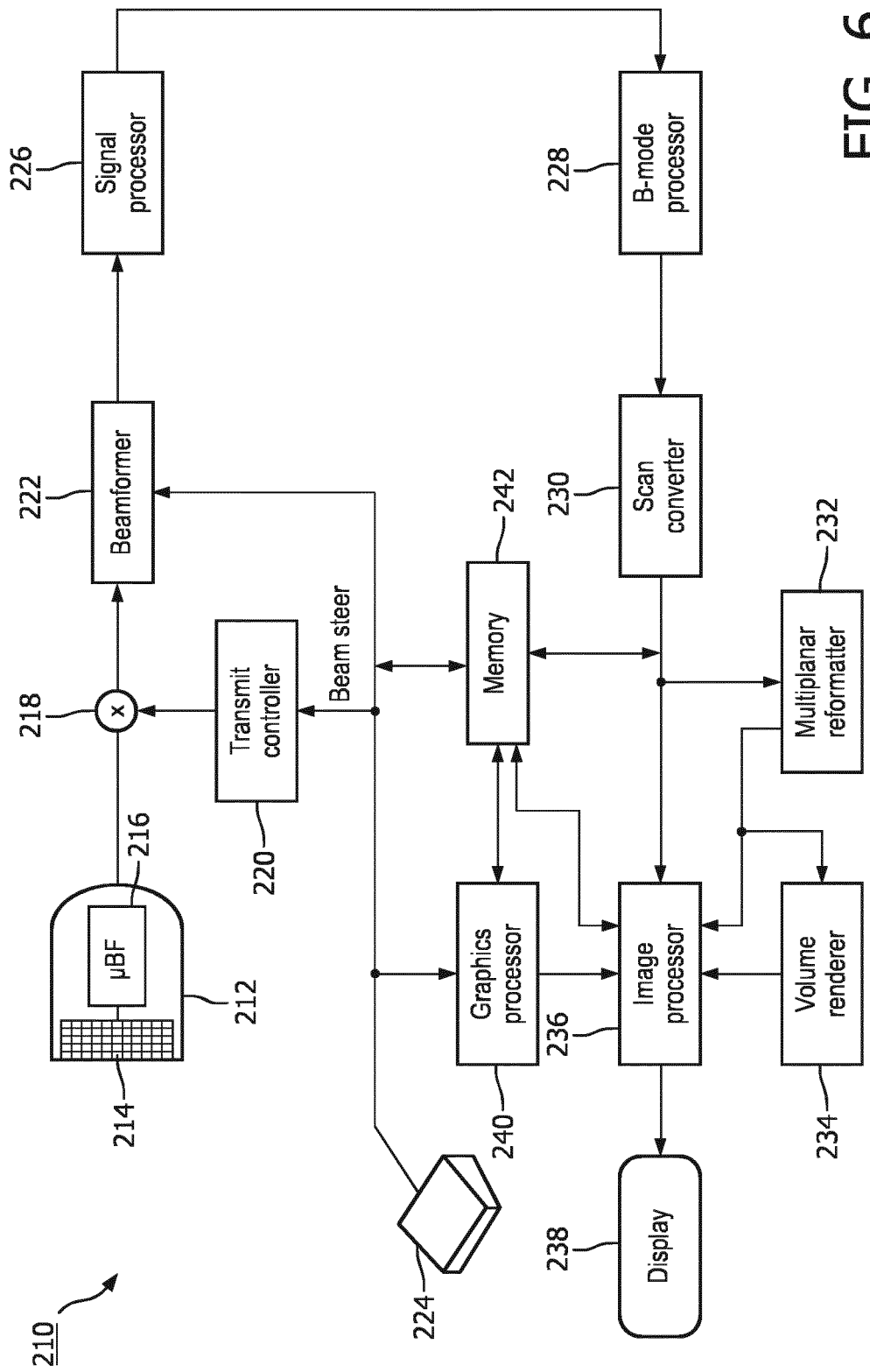
FIG. 6 is a block/flow diagram showing an ultrasound system for acoustically registering ultrasound probes in accordance with one embodiment.

Referring to FIG. 6, an illustrative ultrasound imaging system 210 is shown in block diagram form. The ultrasound system 210 illustratively shows a single transducer device or probe 212, but may include multiple probes 212 or may be employed with other single transducer device or probe 212 systems. The transducer device or probe 212 includes a transducer array 214 for transmitting ultrasonic waves and receiving echo information. The transducer array 214 may be configured as, e.g., linear arrays or phased arrays, and can include piezoelectric elements (PZT), capacitive micromachined ultrasonic transducers (cMUT) elements, etc. The transducer array 214, for example, can include a two or three dimensional array of transducer elements capable of scanning in both elevation and azimuth dimensions for 2D and/or 3D imaging. The probe 212 may include a TTE probe, a TEE probe or any other probe.

The transducer array 214 is coupled to a microbeamformer 216 in the probe 212, which controls transmission and reception of signals by the transducer elements in the array. In this example, the microbeamformer 216 is integrated with the transducer device 212 and is coupled to a transmit/receive (T/R) switch 218, which switches between transmission and reception and protects a main beamformer 222 from high energy transmit signals.

The transmit controller 220, microbeamformer 216 and/or the beamformer 222 control the strength and field of view of transmitted pulses. Adjustments to the strength and the field of view can be made with each cycle or iteration as described with reference to FIG. 3. The calibration module 150 (FIG. 1) in memory 242 provides control signals to the beamformer 222 and/or the transmit controller 220 for this probe 212 (and possibly other probes in the system). In this way, the angle of the field of view and other parameters can be controlled with the system of probes to provide the needed information for synchronously communicating between the probes.

In some embodiments, the T/R switch 218 and other elements in the system can be included in the transducer probe rather than in a separate ultrasound system base. The transmission of ultrasonic beams from the transducer array 214 under control of the microbeamformer 216 is directed by the transmit controller 220 coupled to the T/R switch 218 and the beamformer 222, which may receive input from the user's operation of a user interface or control panel 224 or be preprogrammed and stored in memory 242.

One function controlled by the transmit controller 220 is the direction in which beams are steered. Beams may be steered straight ahead from (orthogonal to) the transducer array, or at different angles for a wider field of view. The partially beamformed signals produced by the microbeamformer 216 are coupled to a main beamformer 222 where partially beamformed signals from individual patches of transducer elements are combined into a fully beamformed signal.

The beamformed signals are coupled to a signal processor 226. The signal processor 226 can process the received echo signals in various ways, such as bandpass filtering, decimation, I and Q component separation, and harmonic signal separation. The signal processor 226 may also perform additional signal enhancement such as speckle reduction, signal compounding, and noise elimination. The processed signals are coupled to a B mode (or other mode: A, M, etc.) processor 228, which can employ amplitude detection for the imaging of structures in the body. The signals produced by the B mode processor are coupled to a scan converter 230 and a multiplanar reformatter 232. The scan converter 230 arranges the echo signals in the spatial relationship from which they were received in a desired image format. For instance, the scan converter 230 may arrange the echo signal into a two dimensional (2D) sector-shaped format, or a pyramidal three dimensional (3D) image. The multiplanar reformatter 232 can convert echoes which are received from points in a common plane in a volumetric region of the body into an ultrasonic image of that plane.

A volume renderer 234 converts the echo signals of a 3D data set into a projected 3D image as viewed from a given reference point. The 2D or 3D images are coupled from the scan converter 230, multiplanar reformatter 232, and volume renderer 234 to an image processor 236 for further enhancement, buffering and temporary storage for display on an image display 238. A graphics processor 240 can generate graphic overlays for display with the ultrasound images. These graphic overlays or parameter blocks may include, e.g., standard identifying information such as patient name, date and time of the image, imaging parameters, frame indices and the like. For these purposes, the graphics processor 240 receives input from the user interface 224, such as a typed patient name. The user interface 224 can also be coupled to the multiplanar reformatter 232 for selection and control of a display of multiple multiplanar reformatted (MPR) images.

In accordance with the present principles, ultrasound data is acquired and stored in memory 242 along with position and orientation data with regards to the positions of the other probes as described, e.g., with the reference to FIG. 1. The memory 242 is depicted as being centrally placed; however, the memory 242 may store data and interact at any position in the signal path.

Figure 7:
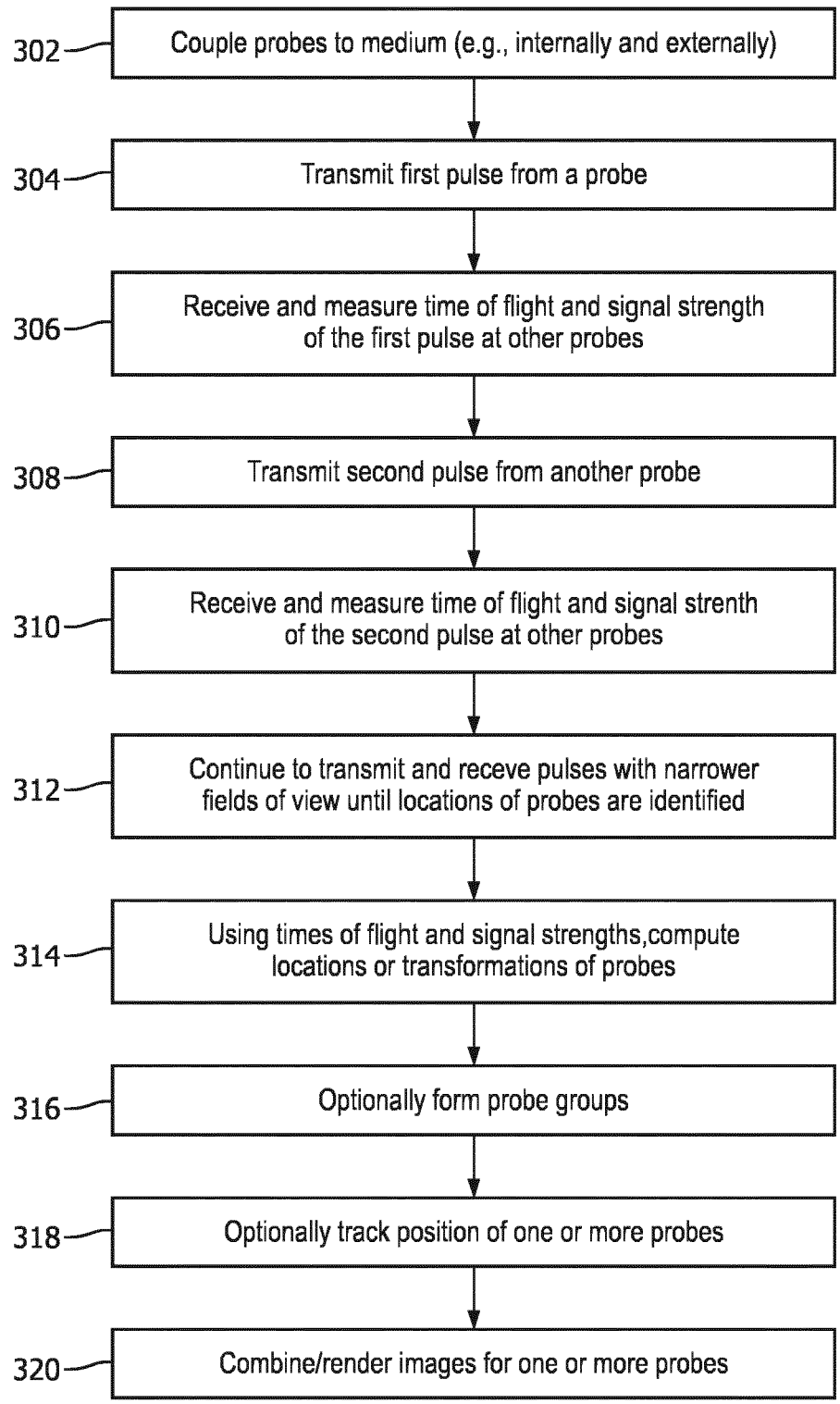
FIG. 7 is a flow diagram showing a method for acoustically registering ultrasound probes in accordance with illustrative embodiments.

Referring to FIG. 7, a method for acoustically registering probes to one another and a common coordinate system is illustratively shown. In block 302, two or more probes (e.g., ultrasound) are coupled to a medium (e.g., a subject or volume). The probes may be different types (e.g., TEE, TTE, etc.) and may be located internally and/or externally to the subject or volume. In block 304, a first acoustic pulse has a first field of view angle set for a first ultrasound probe. The first field of view angle should be wide (the widest for the first iteration). The first field of view angle may be set using a beamformer in the ultrasound device. The first field of view angle may be set using a calibration module. The first field of view angle may be a default number or adjusted and set using user input.

In block 306, the first acoustic pulse is received at a second ultrasound probe (and other probes, if present). The time of flight and signal strength of the first pulse are measured at the first probe using the probes transducer. The time of flight is measured by determining the difference between a time that the first probe initiated the acoustic pulse and a time that the pulse arrived at transducer of the second probe. Signal strength is also measured by the transducer by measuring the power of the signal and comparing the measured power with the power when the acoustic pulse left the first probe.

In block 308, a second acoustic pulse is transmitted from the second ultrasound probe at a narrower field of view angle than the first acoustic pulse. In block 310, the second acoustic pulse is received at the first ultrasound probe (and other probes if present) to measure time of flight and signal strength of the second pulse. In block 312, the transmission and receive iterations between the probes can continue with narrower and narrower fields of view for each cycle. The first ultrasound probe and the second ultrasound probe can have the angle for field of view adjusted using a corresponding beamformer for the probe.

In block 314, the times of flight and signal strengths are recorded and employed to compute positions of the first ultrasound probe and the second ultrasound probe. The first and second probes (and any other probes) are registered to one another and located in a common coordinate system. In one embodiment, a transformation is computed for one or more probes to correlate the location of the probe to one or more other probes and the coordinate system. The first ultrasound probe and the second ultrasound probe (and any other probes) include bandwidths that share one or more frequencies to permit communication therebetween. In one embodiment, the probes may all share a common central frequency.

In some embodiments, in block 316, opposing probes may be grouped into two or more groups. For example, the first ultrasound probe may include a plurality of first ultrasound probes to collectively form a large area probe. Positions are computed for the plurality of the probes in the system based upon measured times of flight and signal strengths to register the probes to each other and the common coordinate system.

In block 318, one of the probes in the system of probes may be tracked and may be employed to define the coordinate system. The probe may be tracked by any suitable technology, e.g., EM tracking, spatial encoding, etc.

In block 320, images are displayed for the data collected for the one or more probes. This may include side-by side displays or compound images generated by fusing or stitching together image data received from the probes into a single image (or multiple images) for display. Ultrasound images and/or information can be combined from all or some probes to display on screen. The images may be combined spatially or temporally depending on the application. For example, images may be stitched together, shown concurrently, shown dynamically (moving over time), etc. Stitching images from one probe into a reference frame of another probe over time can be performed to create a larger image with a larger field of view or to track motion of tissue, provide more detail in an area of interest, etc.

In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for acoustic registration of internal and external ultrasound probes (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An acoustically registerable probe for generating images, comprising:
  a transducer array having a field of view defined by an adjustable field of view angle, the transducer array configured to send and receive acoustic pulses in the field of view;
  a beamformer coupled to the transducer array and configured, in each of a plurality of iterations, to:
    adjust the field of view of the transducer array by iteratively decrementing the field of view angle of the transducer array and adjust signal strength of the acoustic pulses, and
    control the transducer array to send and receive the acoustic pulses, at the decremented field of view angle and the adjusted signal strength, respective to a second acoustically registerable probe configured to generate second images; and
  a processor configured to determine a position of the second acoustically registerable probe based on the decremented field of view angle, time of flight, and the adjusted signal strength of the acoustic pulses in each of the plurality of iterations.

2. The acoustically registerable probe as recited in claim 1, wherein the transducer array is configured to form a large area probe.

3. The acoustically registerable probe as recited in claim 1, wherein the transducer array is configured to generate images that are stitched into a reference frame of the second acoustically registerable probe to create a larger image with a larger field of view.

4. The acoustically registerable probe as recited in claim 1, wherein the processor is configured to indicate a position of the acoustically registerable probe based on the time of flight and the adjusted signal strength of the acoustic pulses.

5. The acoustically registerable probe as recited in claim 4, wherein the processor is configured to decrement the field of view angle of the transducer array at each successive iteration to permit positional identification of the second acoustically registerable probe and/or the acoustically registerable probe.

6. The acoustically registerable probe of claim 1, wherein the beamformer is configured to, in a first iteration of the plurality of iterations, control the transducer array to send and receive the acoustic pulses at a first field of view angle, and
  wherein the processor is configured to determine a direction of the second acoustically registerable probe based on a signal response to the first iteration.

7. The acoustically registerable probe of claim 6, wherein the beamformer is configured to, in a second iteration of the plurality of iterations, control the transducer array to send and receive the acoustic pulses at a second field of view angle, wherein the second field of view angle is narrower than the first field of view angle, and
  wherein the processor is configured to control decrementing of the field of view angle from the first field of view angle to the second field of view angle based on the determined direction of the second acoustically registerable probe.

8. The acoustically registerable probe as recited in claim 1, wherein the second acoustically registerable probe is spaced apart from the acoustically registerable probe in the medium.

9. The acoustically registerable probe as recited in claim 8, wherein a transducer array of the second acoustically registerable probe and the transducer array of the acoustically registerable probe each have a bandwidth that shares one or more frequencies to permit communication therebetween.

10. The acoustically registerable probe as recited in claim 8, wherein the acoustically registerable probe and the second acoustically registerable probe are acoustically registered to a common coordinate system.

11. The acoustically registerable probe as recited in claim 10, wherein the acoustically registerable probe and the second acoustically registerable probe are tracked by a tracking device to register to the common coordinate system.

* * * * *